US008263367B2

(12) United States Patent
Ruan et al.

(10) Patent No.: US 8,263,367 B2
(45) Date of Patent: Sep. 11, 2012

(54) NUCLEIC ACID INTERACTION ANALYSIS (75) Inventors: Yijun Ruan, Singapore (SG); Chialin Wei, Singapore (SG); Melissa Jane Fullwood, Singapore (SG); Jun Liu, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 1083 days.

(21) Appl. No.: 12/020,071

(22) Filed: Jan. 25, 2008

(65) Prior Publication Data
US 2009/0191598 A1    Jul. 30, 2009

(51) Int. Cl.
C07H 22/00 (2006.01)
C12P 19/34 (2006.01)
(52) U.S. Cl. .................................... 435/91.52; 536/23.1
(58) Field of Classification Search .................. None
See application file for complete search history.

(56) References Cited

U.S. PATENT DOCUMENTS

| | | | |
|---|---|---|---|
| 6,054,276 A | 4/2000 | Macewicz | |
| 6,136,537 A | 10/2000 | Macewicz | |
| 6,383,743 B1 | 5/2002 | Kinzler et al. | |
| 6,410,243 B1 | 6/2002 | Wyrick et al. | |
| 6,498,013 B1 | 12/2002 | Velculescu et al. | |
| 2004/0146866 A1 | 7/2004 | Fu | |
| 2005/0059022 A1 | 3/2005 | Ruan et al. | |
| 2005/0255501 A1 | 11/2005 | Ng et al. | |
| 2006/0084111 A1 | 4/2006 | Ruan et al. | |
| 2006/0281097 A1 | 12/2006 | Chiu et al. | |
| 2007/0238101 A1 | 10/2007 | Ruan et al. | |
| 2008/0124707 A1 | 5/2008 | Ruan et al. | |

FOREIGN PATENT DOCUMENTS

| | | |
|---|---|---|
| WO | 0116378 A2 | 3/2001 |
| WO | 0148247 A2 | 7/2001 |
| WO | 0210438 A2 | 2/2002 |
| WO | 0214550 A2 | 2/2002 |
| WO | 2004050918 A1 | 6/2004 |
| WO | 2005007814 A2 | 1/2005 |
| WO | 2005026391 A1 | 3/2005 |
| WO | 2005042781 A2 | 5/2005 |
| WO | 2006003721 A1 | 1/2006 |
| WO | 2006031204 A1 | 3/2006 |
| WO | 2006135342 A1 | 12/2006 |
| WO | 2007004057 A2 | 1/2007 |
| WO | 2007010252 A1 | 1/2007 |
| WO | 2007057785 A2 | 5/2007 |
| WO | 2007091077 A | 8/2007 |

(Continued)

OTHER PUBLICATIONS

Porter et al. (Cancer Research, 2001, 61:5697-5702).*

(Continued)

Primary Examiner — Stephanie K Mummert
(74) Attorney, Agent, or Firm — Rothwell, Figg, Ernst & Manbeck P.C.

(57) ABSTRACT

The present invention provides at least one isolated linear composite nucleic acid molecule comprising at least one first tag from at least one first nucleic acid molecule and at least one second tag from at least one second nucleic acid molecule, wherein the first and second nucleic acids interact in a nucleic acid mixture; and wherein the first and second tags are from different nucleic acid molecules. The invention also provides a method of producing at least one isolated linear composite nucleic acid and to a method of detecting and/or identifying nucleic acid interactions.

16 Claims, 7 Drawing Sheets

FOREIGN PATENT DOCUMENTS

| | | |
|---|---|---|
| WO | 2007106047 A1 | 9/2007 |
| WO | 2007123744 A2 | 11/2007 |

OTHER PUBLICATIONS

Velculescu et al. (Science, 1995, 270, p. 484-487).*

Ng et al. (Curr. Protocol. Molec. Biol, 2007, supplement 79, p. 21.12.1-21.12.42 (or p. 1-42).*

Adams M.D., et al. "Complementary DNA Sequencing: Expressed sequence tags and human genome project", Science, 252(5013):1651-1656 (Jun. 21, 1991).

Brenner S., et al. "In vitro cloning of complex mixtures of DNA on microbeads: Physical separation of differentially expressed cDNAs", PNAS 97(4):1665-1670 (2000).

Brenner S., et al. "Gene expression analysis by massively parallel signature sequencing (MPSS) on microbead arrays", Nat. Biotechnology, 18(6):630-634 (Jun. 2000).

Buck M.J. and Lieb J.D. "ChIP-Chip: considerations for the design, analysis, and application of genome-wide chromatin immunoprecipitation experiments", Genomics, 83(3):349-360 (2004).

Carroll, J. S., et al., "Chromosome-wide Mapping of Estrogen Receptor Binding Reveals Long-range Regulation Requiring the Forkhead Protein FoxA1", Cell, 122:33-43 (Jul. 12, 2005).

Cawley, S., et al., "Unbiased mapping of transcription factor binding sites along human chromosome 21 and 22 points to widespread regulation of noncoding RNAs", Cell, 116:499-509 (2004).

Chiu, K. P., et al., "PET-Tool, a software suite for comprehens ve processing and managing of Paired-End diTag (PET) sequence data", BMC Bioinformatics, 7:390 (2006).

Chum, W.A.Y. and Kwan, H.S., "Modification of Long SAGE for obtaining and cloning long concatemers", BioTechniques, 39(5): 637-640 (Nov. 2005).

Dekker, J., et al., "Capturing chromosome conformation", Science,. 295:1306-1311 (Feb. 15, 2002).

Dostie, J., et al., "Chromosome Conformation Capture Carbon Copy (5C): A massively parallel solution for mapping interactions between genomic elements", Genome Research, 6:1299-1309 (2006).

Dunn, J.J., et al. "Genomic Signature Tags (GSTs): A System for Profiling Genomic DNA", Genome Research, 12 (11):1756-1765 (2002).

Haring, M., et al., "Chromatin immunoprecipitation: optimization, quantitative analysis and data normalization", Plant Methods, 3: 11 (2007).

Hon, W-K., et al., "A Space and Time Efficient Algorithm for Constructing Compressed Suffix Arrays", Algorithmica, .48: 23-36 (2007).

Iyer, V. R., et al., "Genomic binding sites of the yeast cell-cycle transcription factors SBF and MBF", Nature, 409:533-538 (2001).

Johnson, D. S., et al., "Genome-Wide Mapping of in Vivo Prote n-DNA Interactions", Science, 316:1497-1502 (2007).

Klug, S.J. and Famulok, M., "All you wanted to know about SELEX", Molecular Biology Reports, 20:97-107 (1994).

Li, L. and Chandrasegaran, S. "Alteration of the cleavage dillance of Fok I restriction endonuclease by insertion mutagenesis", Proc. Natl. Acad. Sci. USA. 90: 2764-2768 (1993).

Loh, Y-H., et al. "The Oct4 and Nanog transcription network regulates pluripotency in mouse embryonic stem cells", Nature Genetics, 38(4):431-440 (Apr. 2006).

Mathupala, S.P. and Sloan A.E., ""In-gel" purified ditags direct synthesis of highly efficient SAGE Libraries", BMC Genomics, 3:20-24 (2002).

Margulies, M., et al. "Genome sequencing in microfabricated high-density picolitre reactors", Nature, 437:376-380 (2005).

Ng, P., et al. "Gene identification signature (GIS) analysis for trar scriptome characterization and genome annotation", Nature Methods, 2(2):105-111 (2005).

Ng, W.P., et al. "Gene Identification Signature (GIS) Analysis: detailed protocol", 1-14, GIS Analysis protocol, Release NM091204 (2005).

Orlando, V., et al., "Analysis of Chromatin Structure by in Vivo Formaldehyde Cross-Linking", Methods: A companion to methods in Enzymology, 11: 205-214 (1997).

K. Oren, M., "Decision making by p53: life, death and cancer", Cell Death and Differentiation, 10:431-442 (2003).

Peters, B.A. and Velculescu, V.E., "Transcriptome PETs: A genome's best friends", Nature Methods, 2(2):93-94 (Feb. 2005).

Ren, B., et al., "Genome-Wide Location and Function of DNA Binding Proteins", Science, 290:2306-2309 (Dec. 22, 2000).

Roulet, E., et. al. "High-throughput SELEX-SAGE method for quantitative modeling of transcription-factor binding sites", Nature Biotechnology, 20:831-835 (Aug. 2002).

Ruan, Y., et. al. "Interrogating the transcriptome", Trends in Biotechnology, 22(1):23-30 (Jan. 2004).

Shendure, J., et al., "Accurate Multiplex Polony Sequencing of an Evolved Genome", Science, 309:1728-1732 (2005).

Simonis, M., et al., "Nuclear organization of active and inactive chromatin domains uncovered by chromosome conformation capture on-chip (4C)", Nature Genetics, 38(11):1348-1354 (Nov. 2006).

Talbert, P. B. and Henikoff, S. "Spreading of silent chromatin: inaction at a distance", Nature Reviews, 7:793-803 (Oct. 2006).

Taverner, N.V., et al. "Identifying transcriptional targets", Genome Biology. 5(3):210 (2004).

Velculescu, V.E., et al. "Serial analysis of Gene Expression", Science, 270(5235):484-487 (1995).

Wei, C-L., et al. "5' Long serial analysis of gene expression (Long SAGE) and 3' Long SAGE for transcriptome characterization and genome annotation," PNAS, 101(32): 11701-11706 (2004).

Wei, C-L., et al. "A Global map of p53 Transcription-Factor Binding Sites in the Human Genome", Cell, 2006, 124:207-219.

Yamamoto, M. et. al. "Use of serial analysis of gene expression (SAGE) technology", Journal of Immunological Methods, 250:45-66 (2001).

Zhang, Z. and Dietrich, F.S., "Mapping of transcription start sites in *Saccharomyces cerevisiae* using 5' SAGE", Nucleic Acids Research, 33(9):2838-2851 (2005).

Zhao, Z. et al., "Circular chromosome conformation capture (4C) uncovers extensive networks of epigenetically regulated intra- and interchromosomal interactions," Nature Genetics, 38(11):1341-1347 (2006).

Kim, J. et al., "Mapping DNA-protein interactions in large genomes by sequence tag analysis of genomic enrichment", Nature Methods, 2(1):47-53 (2005).

Marinescu, V.D. et al., "START: an automated tool for serial analysis of chromatin occupancy data", Bioinformatics Applications Note, 22(8):999-1001 (2006).

* cited by examiner

After ligation and reversing cross-links.

FIGURE 5

After ligation, reversing cross-links and immobilization to streptavidin beads.

FIGURE 6

After ligation, reversing cross-links, immobilization and ligation to PCR adapters.

Linear interactions

Long linear multimers (interaction noise)

FIGURE 7

After ligation, reversing cross-links, immobilization, ligation to PCR adapters, PCR and size selection.

Linear interactions

SEQUENCE LISTING

```
<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: synthetic oligonucleotide Linker H (first
      strand)
<220> FEATURE:
<221> NAME/KEY: misc_feature
<222> LOCATION: (5)..(5)
<223> OTHER INFORMATION: May be biotinylated

<400> SEQUENCE: 1
gcgatatcgg atccaac                                                  17

<210> SEQ ID NO 2
<211> LENGTH: 21
<212> TYPE: DNA
```

-continued

```
<213> ORGANISM: Artificial Sequence
<220> FEATURE:
<223> OTHER INFORMATION: synthetic oligonucleotide Linker H (second
      strand)

<400> SEQUENCE: 2
gttggatccg atatcgcggc c                                               21
```

NUCLEIC ACID INTERACTION ANALYSIS

FIELD OF THE INVENTION

The present invention generally relates to the field of gene expression. More specifically, the present invention relates to nucleic acid interactions. In particular, the invention relates to analysis, detection and/or identification of nucleic acid interaction components.

BACKGROUND OF THE INVENTION

The study of nucleic acid interactions, in particular interactions in nucleic acid-protein complexes and in chromatin, is important in understanding gene regulation and expression.

Studies of transcription factor binding sites (TFBS) by genome-wide methods such as ChIP-chip (Cawley et al., 2004) and ChIP-PET (Wei et al., 2006), have shown that most TFBS are not located 5' proximal to genes, suggesting extensive remote regulation. While whole genome ChIP methods can identify TFBS, they may be limited in their capability to detect actual interactions between the TFBS, hence other methods are required.

Analysis of these interactions by electron microscopy, light microscopy and fluorescence in situ hybridisation are constrained by technical limitations, such as lack of resolution, or difficulty in preparing samples, and may not provide enough information on these nucleic acid interactions.

In addition, several recently reported methods developed to study these interactions, purported to be high-throughput and/or unbiased, also fall short of expectations.

Dekker et al., (2002) described Chromosome Conformation Capture (3C), to study nucleic acid interactions. As this method requires the use of primers for analysing interactions, some knowledge of the interacting sites is required, and the method is limited to single point detection.

Carroll et al., (2005) described a method coupling ChIP with 3C. This method indicates the nucleic acid molecules which interact with a particular protein of interest, but otherwise faces the same limitations as 3C.

Simonis et al., (2006) described the chromosome conformation capture-on-chip (4C) technique wherein inverse PCR was first performed using primer sequences targeted to specific sites and subsequently, microarray analysis was used to identify other sites (as available on the microarray) which interact with the targeted sites.

Zhao et al., (2006) described a strategy termed circular chromosome conformation capture (4C) wherein the captured sequences which interact with the specific target sequences are identified by sequencing. This method is limited in its application in that only sequences which interact with specific target sequences can be identified.

Dostie et al., (2007) described a strategy termed 5C which includes performing a multiplex ligation-mediated amplification on a 3C library to generate a 5C library to detect global interactions. The 5C forward and reverse primer sequences are designed for all restriction fragments for the genomic region of interest. As a result, the 5C library is a quantitative "carbon copy" of a part of the 3C library, as determined or limited by the 5C primers used. This method is limited in its application in that only interactions between sites corresponding to 5C primers can be identified.

Ruan et al (US 2007-0238101 A1) provides a method utilising ditags capable of high-throughput, global unbiased interrogation of nucleic acid interactions and binding sites. However, in this prior art method, each tag in the ditag is short and occasionally may not be adequate for identification and/or mapping of the interacting fragments. In addition, this prior art method is not able to separate out interactions between different nucleic acid molecules from self-ligated molecules. Further, ditags may also be formed from long linear composite molecules and these may not reflect actual nucleic acid interactions.

Solexa sequencing or sequencing by synthesis is an example of a recently developed sequencing technology (WO 2007/091077, WO 2007/010252 and WO 2007/123744). Solexa sequencing has been applied to the analysis of ChIP sequences but only in the context of comparing immuno-enriched chromatin compared to control chromatin to identify binding sites of a protein known as NRSF (Johnson et al., 2007).

There is thus a need for more efficient methods and robust technologies that may effectively address three-dimensional chromosomal interactions.

SUMMARY OF THE INVENTION

According to one aspect, the invention provides a method of preparing at least one isolated linear composite nucleic acid molecule comprising at least one first tag from at least one first nucleic acid molecule and at least one second tag from at least one second nucleic acid molecule, wherein the first and second nucleic acid molecules interact in a nucleic acid mixture and wherein the first and second tags are from different nucleic acid molecules; comprising the steps of:

(i) providing at least one nucleic acid mixture comprising at least one first nucleic acid molecule interacting with at least one second nucleic acid molecule;

(ii) performing a ligation reaction to ligate the ends of the nucleic acid molecules to form at least one linear composite nucleic acid molecule; and (iii) isolating at least one linear composite nucleic acid molecule comprising at least one first tag from at least one first nucleic acid molecule and at least one second tag from at least one second nucleic acid molecule; wherein the first second tags are from different nucleic acid molecules.

Figure 4:
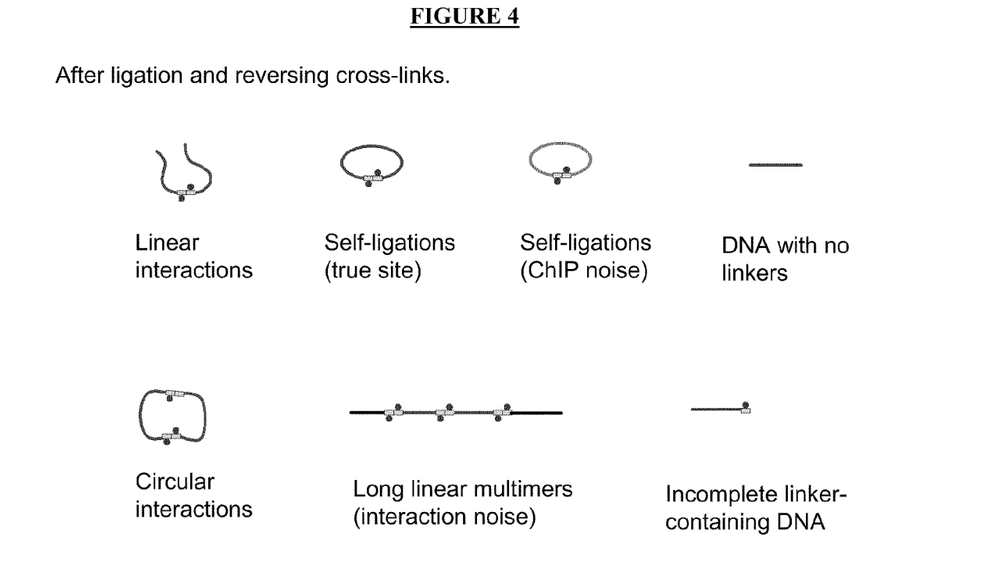
FIG. 4 is a diagram that illustrates examples of molecules which are produced following ligation and reverse cross-linking.

After ligating the ends of the nucleic acid molecules, several types of nucleic acid molecules may be formed. (See FIG. 4 as an example). These include linear composite molecules (linear interactions), circular self-ligated molecules, circular multimers (circular interactions), incompletely ligated and unligated molecules (for example, DNA with no linkers and incomplete linker-containing DNA).

Further, the method according to the invention may separate out and/or provide at least one linear composite nucleic acid molecule or a pool of (more than one) linear composite nucleic acid molecules from the other nucleic acid molecules.

According to another aspect, the method further comprises ligating at least one adapter to at least one end of at least one linear composite nucleic acid molecule to form at least one adapter-ligated linear composite nucleic acid molecule, and isolating the adapter-ligated linear composite nucleic acid molecule(s).

According to another aspect, the present invention provides an isolated linear composite nucleic acid molecule comprising at least one first tag from at least a first nucleic acid molecule and at least a second tag from at least one second nucleic acid molecule, wherein the first and second nucleic acid molecules interact in a nucleic acid mixture; and wherein the first and second tags are from different nucleic acid molecules.

In particular, for each isolated linear composite nucleic acid molecule of the invention, there are at least two tags, with each tag representing a nucleic acid molecule which interacts with a different nucleic acid molecule represented by at least one other tag.

In particular, the nucleic acid mixture comprising interacting nucleic acid molecules comprises at least one nucleic acid-protein complex and/or chromatin. The nucleic acid mixture may be produced by any method. According to one aspect, the nucleic acid mixture may be prepared by chromatin immunoprecipitation (ChIP).

Further, the linear composite nucleic acid molecule(s) of the invention may be amplified. Any standard amplification method may be used, including but not limited to rolling circle amplification and/or polymerase chain reaction (PCR). Further, the linear composite nucleic acid molecule(s) of the invention may also be isolated or purified for further analysis.

According to another aspect of the invention, the linear composite nucleic acid molecules of the invention may be sequenced. The sequence of the tags comprising the linear composite nucleic acid molecules may be obtained by any sequencing method. In particular, the sequencing method used may obtain sequence information from at least two tags of the linear composite nucleic acid molecules.

According to a further aspect, the sequenced tags representing interacting nucleic acid molecules may be mapped to at least one reference sequence. In particular, the reference sequence comprises at least one sequence database, such as a genome sequence database. Mapping the sequenced tags to the genome may determine which nucleic acid molecules interact in close spatial proximity to which other nucleic acid molecules. The interacting nucleic acid molecules identified may be located at some distance on the same chromosome or they may be on different chromosomes. Importantly, the invention accordingly may provide a global de novo picture of these interactions.

Accordingly, the invention may identify and/or discover protein binding site(s) including for example, transcription factor binding sites. In particular, the invention may identify and/or discover sites on different and/or separate nucleic acid molecules which interact with one another and with protein(s) and/or transcription factor(s).

BRIEF DESCRIPTION OF THE FIGURES

FIG. 3 illustrates how non-linker ligated molecules may be eliminated following purification and immobilisation and how circular molecules may be eliminated following adapter ligation and amplification.

FIG. 8 is a diagram illustrating mapping of the tags from the method of the present invention. The vertical lines indicate the sequenced part of the tags that make up the paired tags of the isolated oligonucleotides of the present invention. The sequenced parts of the tags are used for mapping to the reference genome and the sequence is then extended by about 500 bp according to the sequence information of the reference genome to form virtual DNA fragments (firm horizontal lines). As illustrated, it is expected that most of the mapped tags of the invention will identify interactions from distal parts of the same chromosome (cis-interactions) or interactions from different chromosomes (trans-interactions) The dotted horizontal lines indicate the "span" of the interactions. (See boxed mapped interactions in FIG. 8). The mapped tags (not in the box) illustrate that different mapped regions may have different mapped tag densities.

DEFINITIONS

"Adapter" refers to an oligonucleotide molecule which is to be ligated or is ligated to the ends of a nucleic acid molecule. Adapters may be used for amplification, sequencing and/or inserting a nucleic acid fragment into a vector.

"Circular multimer(s)" refer to multimers formed when different or separate nucleic acid molecules are ligated at their ends to form closed nucleic acid molecules. A circular multimer will include at least two separate nucleic acid molecules ligated at the ends to form a closed molecule but may include more than two separate nucleic acid molecules.

"Composite nucleic acid molecule" refers to a nucleic acid molecule comprising at least one first tag from at least one first nucleic acid molecule and at least one second tag from at least one second nucleic acid molecules, wherein the first and second tags are from different nucleic acid molecules. A composite nucleic acid molecule comprises at least two tags, but may comprise three or more tags, with each tag being from a different nucleic acid molecule. A composite nucleic acid molecule may be linear or circular.

A "linear composite nucleic acid molecule" has two free ends, i.e. the ends are not joined together. A linear composite nucleic acid molecule comprises at least two tags, but may comprise three or more tags (multimer), with at least two tags being from different nucleic acid molecules.

"Isolated composite nucleic acid molecule" means a composite nucleic acid molecule which is separated or isolated, and is substantially free of other nucleic acid molecules which are not composite nucleic acid molecules. Isolated composite nucleic acid molecules may comprise at least one composite nucleic acid molecule or may comprise several or many different composite nucleic acid molecules as long as they are substantially free of non-composite nucleic acid molecules. Substantially free is taken to mean at least about 60% free, in particular about 75% free, more in particular about 85%, preferably about 90% free and most preferably about 95%.

"Isolated linear composite nucleic acid molecule" means a linear composite nucleic acid molecule which is separated or isolated, and is substantially free of other nucleic acid molecules which are not linear composite nucleic acid molecules. Isolated linear composite nucleic acid molecules may comprise at least one linear composite nucleic acid molecule or may comprise several or many different linear composite nucleic acid molecules as long as they are substantially free of non-linear composite nucleic acid molecules. Substantially free is taken to mean at least about 60% free, in particular about 75% free, more in particular about 85%, preferably about 90% free and most preferably about 95%.

"Linker" refers to an oligonucleotide molecule which is used to link or links the ends of nucleic acid molecules together. A linker may be used for ligating to another linker to join the ends of nucleic acid molecules.

"Nucleic acid material" comprises nucleic acid molecules.

"Nucleic acid-protein complex" refers to an interaction of nucleic acid material and a protein such as that found in chromatin or when a transcription factor binds to a stretch of nucleic acid.

A "tag" refers to a nucleic acid molecule which represents a larger nucleic acid molecule, such as a gene. The tag may be sequenced and the sequence of the tag may be used to map the tag to a genome. Tags may also be used to identify genes.

"Tag length", in general means the length of a nucleic acid tag comprising a nucleic acid fragment from a longer nucleic acid molecule. The tags of the present invention are generally longer than 19-21 bp. The tags lengths of the linear composite oligonucleotides of the present invention obtained depend on the sonication conditions used and are expected to be at least about 50 bp or longer. However, appropriate sizes of the linear composite suitable for further analysis may be selected for. For example, through size selection of the linear composite nucleic acid molecules, tag lengths about 50-1000 bp may be selected for. In particular, tag lengths of about 50-300 bp long may be selected for. The sizes of the linear composite molecules are longer than the tag lengths. For example, if the tag lenghs are 50-300 bp, the linear composite molecules would be about 200-500 bp (note that the tags are expected to be unequal and have different lengths).

"Virtual DNA fragment" refers to a tag wherein the sequence is extended from the sequenced part of the tag following mapping to the reference genome. Following sequencing, the sequence of the tag is used to map the tag to a reference genome. Once mapped, a virtual DNA fragment is generated by including the sequence from the region it is mapped to for about 500 bp, thus extending the sequence. The direction for extending the sequence information of the tag for the virtual DNA fragment is so as to include the sequence of the part of the tag which is not sequenced, and may be deduced from the method of generating the tag and the sequencing method used. For example, if Solexa sequencing is used, the sequence of the virtual DNA fragment is extended in the same direction as the sequencing method. Further, as another example, the direction for extending the sequence information of a first tag may be towards the adjacent tag ligated to it.

DETAILED DESCRIPTION OF THE INVENTION

The present invention relates to a method of detecting, identifying and/or preparing at least one isolated nucleic acid molecule from a nucleic acid mixture. In particular, the invention provides a method of preparing at least one isolated composite nucleic acid molecule comprising at least one first tag from at least one first nucleic acid molecule and at least one second tag from at least one second nucleic acid molecule, wherein the first and second nucleic acid molecules interact in the nucleic acid mixture and wherein the first and second tags are from different nucleic acid molecules.

According to a first aspect, the invention provides a method of preparing at least one isolated linear composite nucleic acid molecule comprising at least one first tag from at least one first nucleic acid molecule and at least one second tag from at least one second nucleic acid molecule, wherein the first and second nucleic acid molecules interact in a nucleic acid mixture and wherein the first and second tags are from different nucleic acid molecules; comprising the steps of:

(i) providing at least one nucleic acid mixture comprising at least one first nucleic acid molecule interacting with at least one second nucleic acid molecule;

(ii) performing a ligation reaction to ligate the ends of the nucleic acid molecules to form at least one linear composite nucleic acid molecule; and (iii) isolating at least one linear composite nucleic acid molecule comprising at least one first tag from at least one first nucleic acid molecule and at least one second tag from at least one second nucleic acid molecule; wherein the first and second tags are from different nucleic acid molecules.

According to a second aspect, the present invention also provides an isolated linear composite nucleic acid molecule comprising at least one first tag from at least one first nucleic acid molecule and at least one second tag from at least one second nucleic acid molecule; wherein the first and second nucleic acid molecules interact in a nucleic acid mixture; and wherein the first and second tags are from different nucleic acid molecules.

The nucleic acid mixture may comprise at least one nucleic acid-protein complex and/or chromatin. The nucleic acid mixture may be prepared by any method. In particular, the nucleic acid mixture may be prepared by a modified chromatin immunoprecipitation (ChIP). A standard ChIP protocol (Orlando et al., 1997) may be used for obtaining the chromatin but with some modifications. In particular the modifications are that the nucleic acid material is not eluted, reverse cross-linked to remove the formaldehyde cross-links or purified. The chromatin prepared by this method may be bound to sepharose beads or any other suitable type of beads.

Sonication may be used to break up long nucleic acid molecules into separate molecules, however, the nucleic acid interactions are retained because of the cross-linking. In this way, interacting nucleic acid sites which are widely separated on the same long nucleic acid molecules are broken into separate molecules and may be identified by the method of the invention.

The ends of the nucleic acid molecules in the chromatin are then end-filled, for example by T4 DNA polymerase. A ligation reaction is then performed to ligate the ends of the nucleic acid molecules together.

This may involve a "first ligation" step comprising ligating linker(s) with at least one non-ligatable end to at least one end of the nucleic acid molecule(s). After the first ligation, excess linkers may be removed and the ligated linker(s) may be converted to make the non-ligatable end(s) ligatable. The linker(s) are then ligated, thus linking the ends of the nucleic acid molecules to form at least one linker-ligated linear composite molecule.

The following are non-limiting examples of linkers which may be used for ligating or linking the ends of the nucleic acid molecules.

```
Linker H (first strand):
5' GCG ATA TCG GAT CCA AC 3'        (SEQ ID NO: 1)

Linker H (second strand):
5' GTT GGA TCC GAT ATC GCG GCC 3'   (SEQ ID NO: 2)
```

The first strand and second strand of linker H forms the linker H with an overhang:

```
5'      GCGATATCGGATCCAAC 3'
3' CCGGCGCTATAGCCTAGGTTG       5'
```

The blunt end is for ligating to the ends of the nucleic acid molecules while the overhang is for ligating with another linker, thus joining the ends of the nucleic acid molecule.

Figure 1:
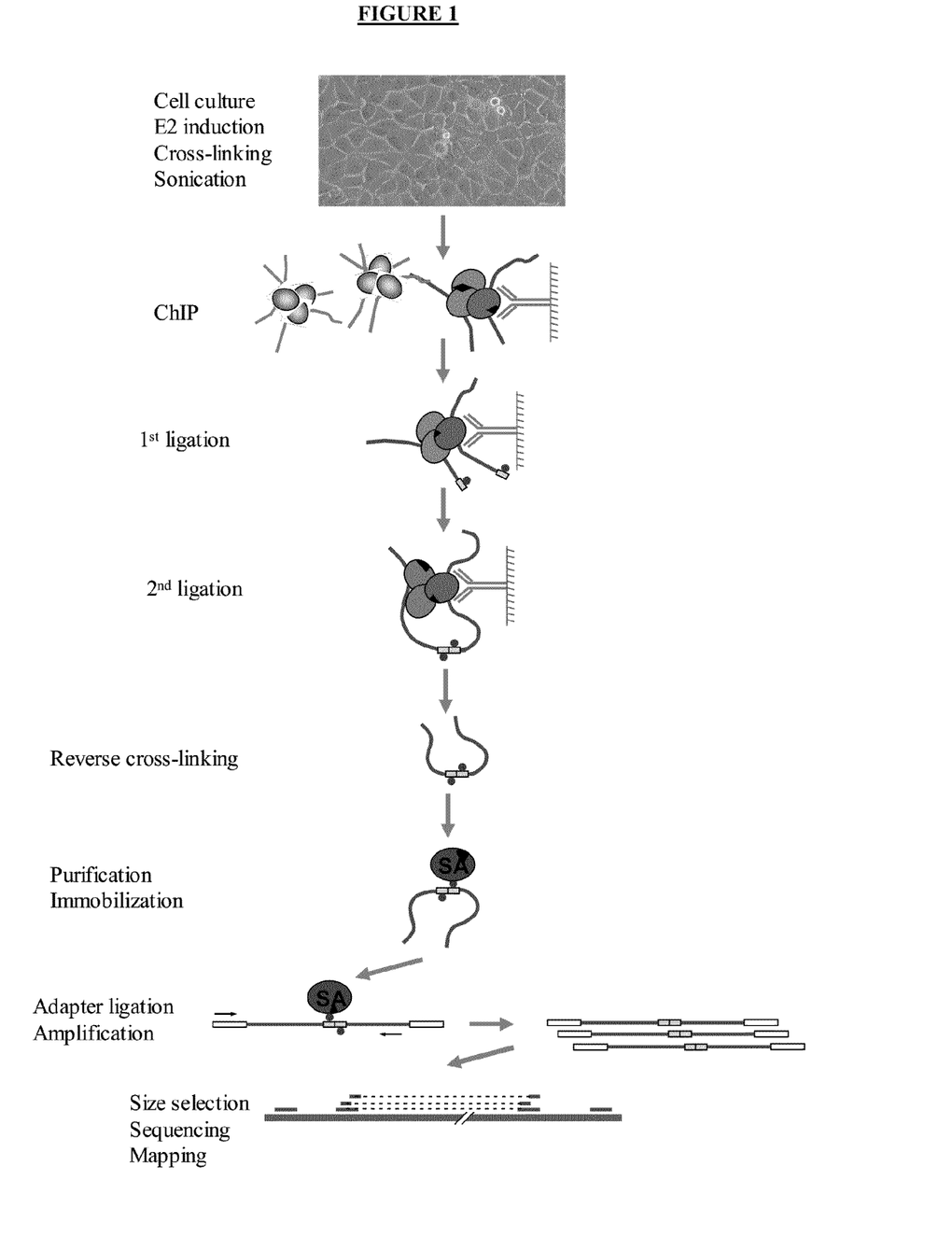
FIG. 1 is a diagram which illustrates an example of the method and the isolated oligonucleotide(s) of the invention.
Figure 2:
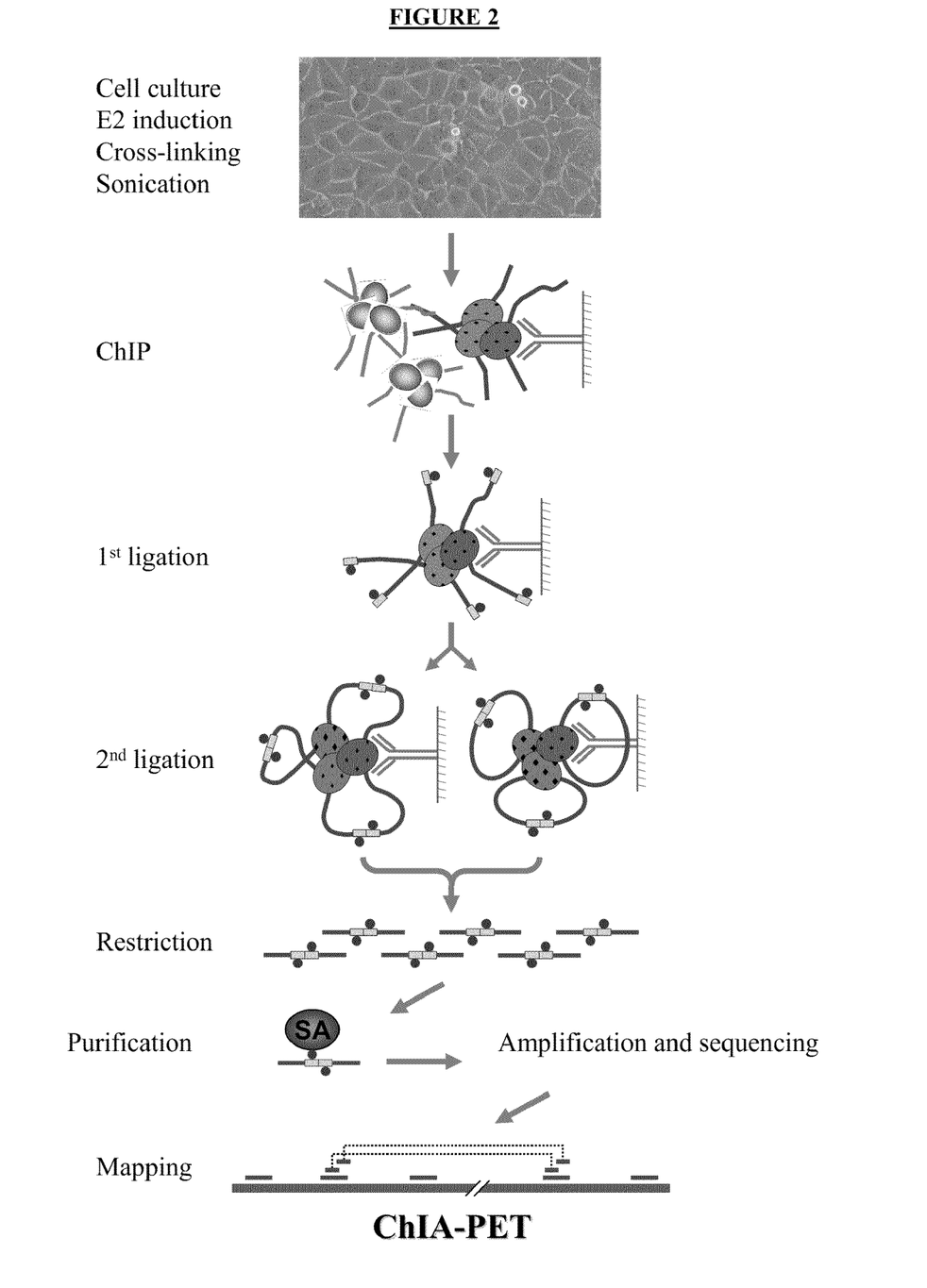
FIG. 2 is a diagram which illustrates in general the nucleic acid interaction analysis method of Ruan et al., (US application 2007-0238101 A1). This method available in the prior art generally results in short ditags because the tags are generated following restriction. In addition, these tags also include tags obtained as a result of self-ligation or circularisation of the same nucleic acid molecule.

For example, at least one dephosphorylated linker may be ligated to at least one end of the nucleic acid molecules, as shown in FIG. 1. The linker(s) may be coupled to biotin for subsequent purification with avidin or streptavidin. It is understood that the linker(s) are not limited to being coupled to biotin molecules and may be coupled to any other component. In particular, the component may be used to purify or isolate the linker-ligated nucleic acid molecules.

In one non-limiting embodiment, the fifth base, T (in bold) of the first strand of Linker H (SEQ ID NO: 1) is biotinylated.

The ligation conditions may be modified or adjusted, as required, so as to maximise the ligation of the linker(s) to the end(s) of the nucleic acid molecules, or to optimize other conditions relevant to particular embodiments. Any ligation condition may be modified or adjusted, including but not limited to increasing or decreasing the time for the ligation reaction and/or concentration of the reagents. Following the first ligation, the nucleic acid molecules may be eluted off the sepharose beads. Alternatively, they may also be left on the beads.

As the linker(s) are dephosphorylated, it is expected that the linker(s) are unliklely to ligate to form dimers or concatemers of linker(s).

In addition, since the linker(s) are dephosphorylated, it is expected that the linker(s) may ligate to the phosphorylated ends of the nucleic acid molecule but cannot ligate to link together the ends of the nucleic acid molecule until they are phosphorylated.

The dephosphorylated ends of the ligated linker(s) are then phosphorylated. Following this, a second ligation is performed, to allow the ends of the nucleic acid molecules to ligate. The ligation conditions may be modified or adjusted as required, so as to maximise the ligation of the ends of different nucleic acid molecules via the linkers to form linear nucleic acid molecules and to reduce the self-ligation or circularisation of the ends of any one nucleic acid molecule and/or formation of circular multimers. Any of the ligation conditions may be modified, including but not limited to increasing or decreasing the time for the ligation reaction and/or concentration of the reagent(s). In other words, the ligation reactions are adjusted or modified to maximise intermolecular ligation of separate nucleic acid molecules. In particular, the ligation is performed under very dilute conditions of the nucleic acid molecules to maximise the ligation of the ends of different nucleic acid molecules and to reduce the formation of circular multimers.

Alternatively, at least one dephosphorylated linker comprising at least one restriction enzyme site may be ligated to at least one end of the nucleic acid molecules in the nucleic acid mixture. This is followed by cutting the ligated linker(s) to produce ligatable ends. The ligatable ends of the ligated linker(s) may then be ligated to ligate the ends of the nucleic acid molecules. The ligatable end after restriction may be a blunt or have a cohesive end with a 5' or 3' overhang. In particular, a restriction enzyme which cuts rarely may be used. In other words, the restriction site for the enzyme should not occur too frequently. The reason being, to reduce the possibility of cutting the nucleic acid material in the nucleic acid mixture to very short fragments.

Accordingly, the ligated nucleic acid molecule(s) may comprise at least one linker linking the first nucleic acid molecule and the second nucleic acid molecule.

Following the second ligation, the nucleic acid material is then treated to reverse the formaldehyde cross-links and purified. Purification of at least one linker-ligated nucleic acid molecule may be performed using a binding system comprising at least two components, where in at least one first component is coupled to the linker, and at least a second component binds the first component to isolate the linker-ligated nucleic acid molecule(s). The components include but are not limited to streptavidin-biotin, avidin-biotin, protein-antibody and/or magnet/magnetic material.

In particular, biotinylated linker-ligated nucleic acid material is purified using streptavidin beads. Only the nucleic acid material that contains biotinylated linkers will be immobilized on the streptavidin beads. If another component is bound to the linkers used, other systems of purifying the nucleic acid molecules suitable for the component may be used.

Following purification, adapters may then be ligated to the ends of the purified nucleic acid material (See FIG. 1). As can be understood from FIG. 3, only blunt ended, non-circularised nucleic acid material can be ligated to the adapters. Self-ligated nucleic acid molecules and circular multimers cannot be ligated to the adapters. The linear composite nucleic acid molecule(s) with both adapters and linkers ligated may then be isolated.

Either the linker or the adapters or both may be coupled to at least one first component(s). The coupled component(s) may be used to isolate ligated nucleic acid material. In particular, the coupled component(s) may be used to isolate linear composite nucleic acid molecule(s). The coupled first component(s) bind to at least one second component(s) which may be used to isolate nucleic acid molecule(s) which are coupled to the first component(s).

The components may include but are not limited to streptavidin-biotin, avidin-biotin, protein-antibody and/or magnet/magnetic material.

Accordingly, the method is able to obtain at least one isolated linear composite nucleic acid molecule comprising at least one first tag from at least one first nucleic acid molecule and at least one second tag from at least one second nucleic acid molecule, wherein the first and second nucleic acid molecules interact in a nucleic acid mixture, and wherein the first and second tags are from different nucleic acid molecules. In addition, the isolated linear composite nucleic acid molecule(s) may further comprise adapters.

The isolated linear composite molecule(s) may comprise at least one linker linking the tags and/or at least one adapter. Either the linker(s) and/or adapters may be biotinylated or coupled to another component for use in purifying or isolating the linker-ligated and/or adapter ligated linear composite nucleic acid molecule(s).

Figure 5:
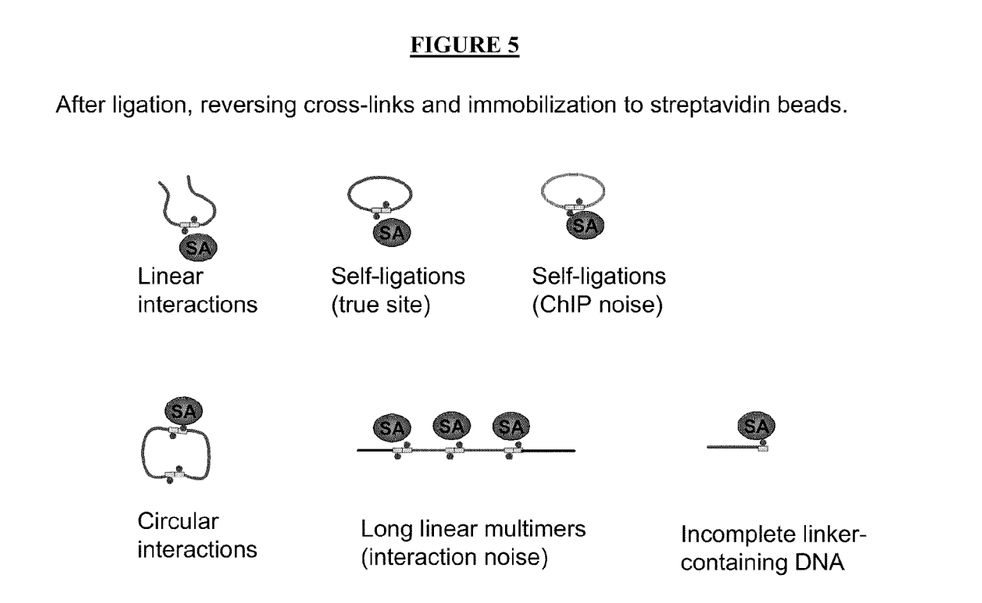
FIG. 5 is a diagram that illustrates examples of molecules which are retained after immobilisation to streptavidin beads (SA).

The method of the invention does not isolate interacting nucleic acid ligated to form circular multimers (circular interactions in FIG. 5). However, it is expected that the number of non-circular ligations is high, and with careful adjustment of the ligation conditions, it may be possible to maximise the ligation of the ends of separate nucleic acid molecules and reduce circularisation of the ends of any one nucleic acid molecule and/or formation of circular multimers.

Further, it is expected that the method should not produce substantial bias as there is no aspect of the method that will make it more likely that DNA species of a particular type will only form circular interactions instead of linear interactions. In addition, while PCR of fragments of different lengths may result in a length bias, the size range of the fragments used in this protocol is small. In addition, sonication tends to produce mostly random breaks in the DNA, hence sonication will tend to have an equal chance of producing short or long fragments.

In addition, the method of the invention generates nucleic acid molecules comprising longer tags than the nucleic acid interaction analysis method disclosed in Ruan et al., (US 2007-0238101 A1). The tag length of the linear composite nucleic acid molecules are expected to be longer than 19-21 bp in length. The tag lengths in the linear composite molecules are dependent on the sonication conditions used. In general, the tag lengths of the linear composite molecules may be at least about 50 bp or longer. Linear composite molecules of suitable sizes for further analysis may be selected for using size selection methods known to the person skilled in the art. For example, through size selection of the linear composite nucleic acid molecules, tag lengths about 50-1000 bp may be selected for. In particular, tag lengths of about 50-300 bp long may be selected for.

Figure 6:
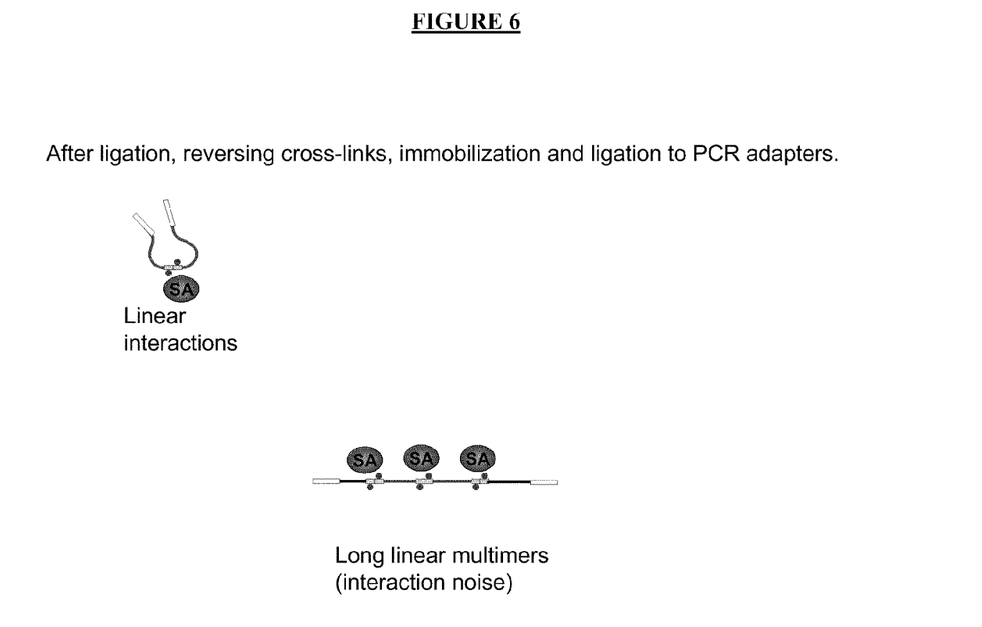
FIG. 6 is a diagram that illustrates examples of molecules following ligation to adapter and amplification.

According to a further aspect of the invention, PCR may be performed to amplify the linear composite nucleic acid molecules. The linear composite nucleic acid molecules, before or after amplification, may be selected for suitable sizes, by any standard method, including gel electrophoresis and gel excision. The main considerations in selection for the appropriate sizes of the linear composite nucleic acid molecules are that the sizes should be above the size of primer dimers and unannealed adapters and below the sizes of long linear multimers. Long linear multimers are undesirable because they may complicate the data analysis. Long multimers are chimeras and may comprise several linear composite molecules linked together (FIG. 6). They represent false interactions and accordingly are regarded as "interaction noise" (FIG. 6). Moreover, long linear multimers may result from the ligation of several nucleic acid molecules and accordingly may represent false interactions. In particular, linear composite nucleic acid molecules with sizes of approximately 200-500 bp may be selected. (The tag length of each tag in the linear composite nucleic acid molecules are unequal and about 50-300 bp). Further, if the ligation reactions are optimised such that long linear multimers are formed only with a low frequency, it may be possible that larger sized fragments of linear composite nucleic acid molecules may be selected. Accordingly, with size selection, an advantage is that long linear multimers may be eliminated as their sizes will be above the size range. Similarly, fragments that are too short, unannealed adapters and primer dimers may also be eliminated.

In addition, the linear composite nucleic acid molecules may be concatenated by standard methods. In particular, the length controlled concatenation method (Ruan et al., U.S. application Ser. No. 11/449,872) may be used.

According to yet another aspect of the invention, the isolated linear composite nucleic acid molecules may be sequenced. In particular, the sequencing method used may obtain sequence information from different regions of the nucleic acid molecule, for example, from at least two tags of the linear composite nucleic acid molecule.

For example, the isolated nucleic acid molecules may be sequenced according to the Solexa method (llumina) which is capable of pairwise sequencing two different regions of a target nucleic acid molecule. Accordingly, the Solexa method may be adapted for sequencing at least two different tags from each linear composite molecule However, other known sequencing methods, including but not limited to Sanger sequencing, 454 sequencing, sequencing by ligation (Applied Biosystems SOLiD system) and the true single molecule sequencing (Helicos Biosciences Corporation) may also be used.

The Solexa method is a technology that can provide ultra-high output sequencing of paired tags from the isolated oligonucleotides (WO 2007/010252, WO 2007/091077 and WO 2007/123744), the entire contents of which is herein incorporated by reference. The method, also known as Sequencing by Synthesis, basically involves the following steps: (1) fragmentation of the DNA; (2) ligation of adapters to both ends of the fragments; and (3) attachment of single stranded fragments randomly to the inside surface of a flow cell.

Following this, (4) bridge amplification is performed. The bridge amplification involves (a) allowing single stranded fragments to bend to come into contact with primers randomly bound on the inside surface of the flow cell, (b) single stranded fragments becoming double stranded fragments, which are then (c) denatured. Cycles of amplification are repeated such that millions of clonal clusters of double stranded DNA are generated in each channel of the flow cell, (5) Sequencing is then performed, using reversible, fluorescent terminators and polymerase.

Solexa sequencing is ultra-high output in the sense that it can sequence many different molecules concurrently and hence generate a large quantity of sequence information and is suitable for use with the method of the present invention.

The method of the invention provides linear composite nucleic acid molecules comprising longer tags (in particular, selected to be about 50-300 bp) than the nucleic acid interaction analysis method disclosed in Ruan et al., (US 2007-0238101 A1). The tag length of the linear composite nucleic acid molecules are expected to be longer than 19-21 bp in length. In particular, the tag lengths about 50-300 bp are selected for.

The linear composite nucleic acid molecules comprising the longer tags may accordingly be sequenced directly by the high-throughput Solexa method according to the manufacturer's instructions.

The Solexa method has several important advantages: (1) the Solexa method can sequence "tags" of 20-36 base pairs per read presently. This tag length may also increase with further technology improvements (2) Solexa may be capable of sequencing tags from both sides of the DNA fragment, providing paired end tag information (3) Solexa is capable of performing reads on long DNA fragments of variable length.

Solexa sequencing may be carried out directly on the nucleic acid molecules of the invention by ligating adapters which are also Solexa adapters or primers to the nucleic acid molecules. The invention therefore provides a streamlined method wherein the isolated linear composite nucleic acid molecules may directly be used for the high-throughput Solexa sequencing method.

The whole sequencing process is computerised, and many sequencing reactions occurring in parallel on the surface may be detected. (WO 2007/123744).

It is understood that other sequencing methods may also be used for sequencing the isolated linear composite nucleic acid molecules. In particular, sequencing methods capable of sequencing from at least two different regions of the nucleic acid molecules, for example, from two tags of the linear composite nucleic acid molecules may be used. As alternative examples, multiplex polony sequencing (Shendure et al., 2005), mate-paired sequencing with the Applied Biosystems SOLiD system and paired end sequencing using the Heliscope Single Molecule Sequencer (Helicos Biosciences Corporation) may also be used to sequence the linear composite nucleic acid molecules. Mate-paired sequencing may be carried out using the SOLiD Mate-Paired Library Sequencing Kit (Applied Biosystems).

Following sequencing, each tag of the linear composite nucleic acid molecules can then be mapped to the genome. The method produces nucleic acid molecules comprising longer tags (in particular, selected to be about 50-300 bp in length) which may be mapped accurately to the genome. Since the tags are longer, the rate at which the tags may map uniquely to the genome is expected to be high. Each single tag may be used to identify binding sites. Paired tags from each isolated nucleic acid of the invention may be used to identify nucleic acid interactions, particularly interactions between binding sites of proteins in nucleic acid-protein complexes.

The invention provides isolated linear composite nucleic acid molecules comprising tags from at least two different or separate interacting nucleic acid molecules, and therefore eliminates nucleic acid molecules comprising tags from the ends of the same nucleic acid molecule ligating together. Such self-ligated nucleic acid molecules being circular are not present in the material for sequencing. Accordingly, following sequencing and subsequent mapping, only tags representing different or separate interacting nucleic acid molecules are obtained. (See FIG. 7). The "noise" from sequences contributed by self-ligated nucleic acid molecules and long linear multimers is reduced.

This can be better understood as discussed below with reference to FIGS. 3-7. Following ligation and reverse cross-linking steps shown in FIG. 3, linear interactions, self-ligations (true site), self-ligations (ChIP noise), DNA with no linkers, cicurlar multimers (circular interactions), long linear multimers and incomplete linker-containing DNA are obtained (See FIG. 4).

Figure 3:
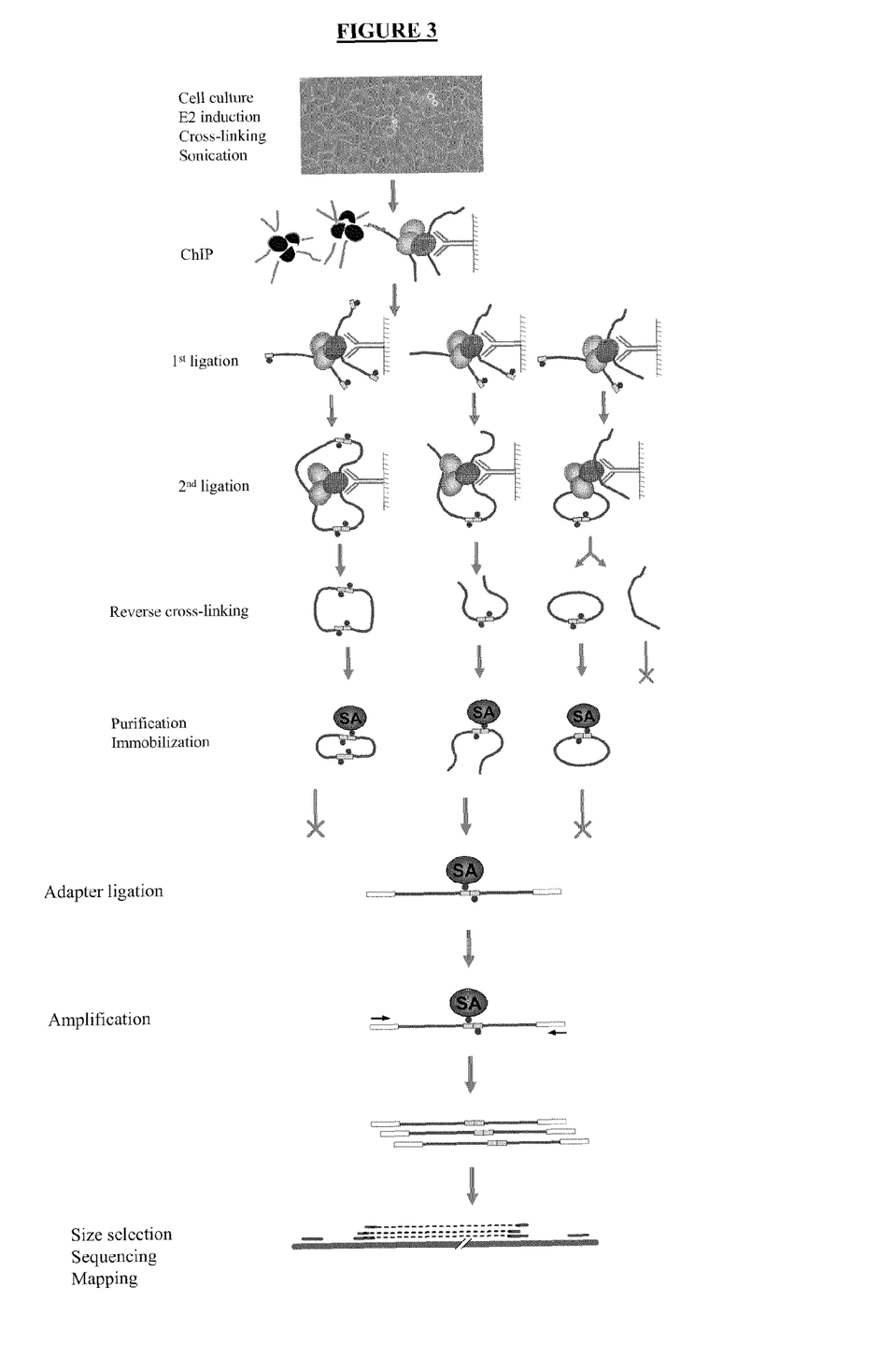
FIG. 3 is a diagram which illustrates an example of the method of the invention. In particular.

DNA with no linkers may be eliminated during the purification and immobilisation step (see FIG. 3 and FIG. 5).

Self-ligation (true site) of a nucleic acid molecule comprises a site that interacts with a particular protein of interest but it only represents a single site interaction. Self-ligation (ChIP noise) on the other hand, is a false negative piece of nucleic acid molecule which does not interact with the particular protein of interest at all and can be regarded as a "contamination" of the ChIP preparation. As the method of the invention provides for studying interactions of sites located at great distances or on different molecules, these self-ligated molecules may be eliminated because adapters may not be ligated to them and accordingly, they may also not be amplified by PCR. (See FIG. 6).

In addition, although incomplete linker-containing DNA are also obtained after immobilisation to streptavidin beads (See FIG. 5), it is likely that the presence of the strepavadin bead provides a hindrance to the ligation of adapters to one end of these molecules and these molecules may not be amplified by PCR during the next step. Further, a possible reason why there is incomplete ligation of the linker with another linker on these molecules is because of an incomplete reversal of the reaction to make the ends ligtable. It follows that these molecules may also not ligate to the adapters and hence may not be amplified (See FIG. 6).

Figure 7:
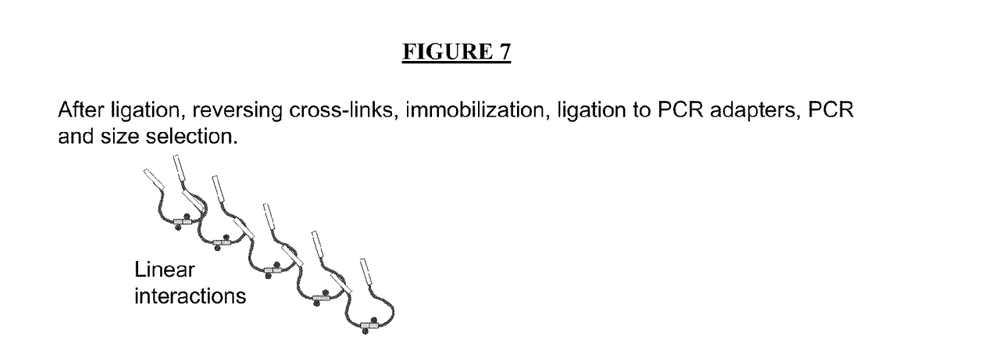
FIG. 7 is a diagram that illustrates the molecules which represents linear interactions of nucleic acid molecules after size selection.

After amplification by PCR (FIG. 3), both linear interactions and long linear multimers may be obtained (FIG. 6). However, long linear multimers may be eliminated by size selection (FIG. 7). Size selection of nucleic acid molecules may be carried out by any standard method, including gel electrophoresis and gel excision.

The present invention allows the study of global nucleic acid interactions de novo without limitation to the primers or microarrays used. However, the prior art methods utilising primers may require initially an assumption of interactions (pre-conceived surmise) and may not be truly global, since the construction of primer pairs representing a global perspective of the reference genome is impractical. The present invention accordingly provides a method capable of studying global nucleic acid interactions, with longer tags representing nucleic acid interactions and a reduction in "noise".

Having now generally described the invention, the same will be more readily understood through reference to the following examples which are provided by way of illustration, and are not intended to be limiting of the present invention.

EXAMPLES

Standard molecular biology techniques known in the art and not specifically described were generally followed as described in Sambrook and Russel, Molecular Cloning: A Laboratory Manual, Cold Springs Harbor Laboratory, New York (2001).

Example 1

Chromatin Immunoprecipitation

Cells were grown harvested, formaldehyde cross-linked and chromatin immunoprecipitated according to standard procedures with slight modifications (see, for example Orlando et al., 1997). However, following the last wash with TE buffer, the material is not eluted from the beads, reverse cross-linked or purified. Instead the material is diluted 1 in 2 and stored at 4° C. until use.

As a control, an aliquot was taken and subjected to elution and reverse cross-linking according to the standard protocol (Orlando et al., 1997). The amount of DNA may be determined according to any standard protocol. The aliquot may also be checked for proper ChIP enrichment according to standard protocols (Haring et al., 2007).

Example 2

End Filling Nucleic Acid Fragments with T4 DNA Polymerase

Following ChIP, the beads were resuspended by pipetting. A volume of beads suspension corresponding to ~100 ng of ChIP DNA, as determined from the DNA quantitation was used for end filling. This volume of beads were collected by centrifugation at 100 g for 5 minutes and resuspended in 150 µl of sterile distilled water.

The reaction mix was prepared as follows:

| | |
|---|---|
| Beads | 150 µl |
| 10x Buffer for T4 DNA Polymerase (Promega) | 50 µl |
| 10 mM dNTPs (Eppendorf) | 5 µl |
| T4 DNA Polymerase (Promega, 7.9 u/ul) | 6.3 µl |
| Sterile distilled H$_2$O | 438.7 µl |
| | 500 µl |

The reaction was then incubated at 37° C. for 15 minutes with gentle mixing on a rotator. (Intelli-Mixer RM-2L, Skyline). In particular, the manufacturer's pre-program F8 (30 rpm) may be used.

Following the reaction, the beads were washed thrice with 1 ml Wash buffer (10 mM Tris-Cl, pH 7.5; 1 mM EDTA; 500 mM NaCl, all reagents from Ambion). The beads were mixed well by inverting the microfuge tubes and collected by centrifugation at 100 g for 5 minutes at 4° C.

Following the last wash, the beads were collected for use in ligation of biotinylated linkers.

Example 3

Ligation of Dephosphorylated Biotinylated Linkers

The reaction mix was prepared as follows.

| | |
|---|---|
| Biotinylated linkers (200 ng/µl) (IDT) | 10 µl |
| 5x T4 DNA Ligase Buffer with PEG (Invitrogen) | 200 µl |
| T4 DNA Ligase (30 u/ul, Fermentas) | 4 µl |
| H$_2$O | 86 µl |
| | 1000 µl |

The final concentration of T4 DNA ligase was at ≧0.1 u/µl. Following the final wash from above, the beads were suspended in this reaction mix and incubated at 16° C. with gentle mixing on a rotator (Intelli-Mixer RM-2L, Skyline) for 16 hours. The manufacturer's pre-program F8 (30 rpm) may be used.

Following the ligation, the beads were washed three times as described in Example 2 to remove the excess linkers.

Example 4

Phosphorylation of Linkers

The reaction mix was prepared as follows:

| | |
|---|---|
| 10x T4 DNA Ligase Buffer (NEB) | 100 µl |
| T4 DNA Polynucleotide Kinase (10 u/µl, NEB) | 20 µl |
| Sterile distilled H$_2$O | 880 µl |
| | 1000 µl |

The washed beads from the ligation reaction were resuspended in the above reaction mix and incubated at 37° C. with gentle mixing on a rotator (Intelli-Mixer RM-2L, Skyline) for 30 minutes. In particular, the manufacturer's pre-program F8 (30 rpm) may be used.

Example 5

Second Ligation Reaction

The second ligation reaction was performed to ligate the phosphorylated linkers by adding 6 µl of T4 DNA Ligase (30 U/µl, Fermentas). The contents were mixed immediately and incubated at 22° C. with gentle mixing on a rotator (Intelli-Mixer RM-2L, Skyline) for 16 hours. In particular, the manufacturer's pre-program F8 (30 rpm) may be used.

Example 6

Elution and Reverse-Crosslinking

Following ligation, the ligation reaction was separated into 575 µl aliquots, with adjustment to the required volume using sterile distilled water if necessary. 150 µl of Elution buffer (1% SDS, 0.1M NaHCO$_3$) and 5 µl of proteinase K (Ambion, 20 mg/ml) were added to each aliquot and the beads were incubated at 65° C. overnight to remove the cross-links and elute the nucleic acid molecules.

Example 7

DNA Purification

The solution was then centrifuged at 16,100 g for 2 minutes and the supernatant was transferred into new microfuge tubes. The DNA was extracted using phenol: chloroform: isoamyl alcohol (25:24:1), pH7.9 (Ambion). Alternatively, a phase-gel tube (Eppendorf) may be used to extract the DNA.

The DNA was further purified using sodium acetate and isopropanol precipitation as follows:

| | |
|---|---|
| DNA (after phenol extraction) | ~500 µl |
| 3M NaOAc, pH5.2 (Ambion) | 50 µl |
| GlycoBlue (15 mg/ml) (Ambion) | 2 µl |
| Isopropanol (−20° C.) (Sigma) | 500 µl |

The reaction was incubated at −80° C. for 1 hour and the DNA precipitate was obtained by centrifugation at 16,100 g at 4° C. for 30 minutes. The DNA pellet obtained was washed twice with 500 µl of 75% ethanol and resuspended in 30 µl of EB buffer (Qiagen).

Example 8

Preparation of Dynabeads

50 µl of resuspended Dynabeads M-280 Streptavadin (10 mg/ml), (Invitrogen) were transferred to a 1.5 ml microfuge tube using a magnetic particle collector (Invitrogen) according to the manufacturer's instructions. The beads were washed twice with 2×B&W buffer (10 mM Tris-HCL pH 7.5, 1 m M EDTA, 2 M NaCl) and resuspended in 30 µl of 2×B&W buffer.

Example 9

Immobilization of the Nucleic Acid Molecules Comprising the Paired Tags

30 µl of the DNA (from Example 7) was added to the resuspended Dynabeads prepared from above and mixed well. The mixture was then incubated at 22° C. with gentle mixing on a rotator (Intelli-Mixer RM-2L, Skyline) for 30 minutes. In particular, the manufacturer's pre-program F8 (30 rpm) may be used. The beads were washed twice with 100 µl of 1×B&W buffer (5 mM Tris-HCL pH 7.5, 0.5 mM EDTA, 1 M NaCl). The Dynabeads were collected during each wash with a Magnetic Particle Collector (Invitrogen).

Example 10

Ligation of Solexa Adapters to the Immobilised Nucleic Acid Molecules

The A-tailing of the DNA as well as the ligation of Solexa adapters (Illumina) to the immobilised nucleic acid molecules was performed using the Solexa/Illumina Paired End Sample Prep Kit iten #1001809 according to the manufacturer's instructions except that the beads were washed twice after each enzymatic reaction with 100 µl of 1×B&W buffer (5 mM Tris-HCL pH 7.5, 0.5 mM EDTA, 1 M NaCl). The Dynabeads were collected during each wash with a Magnetic Particle Collector (Invitrogen).

Example 11

Polymerase Chain Reaction (PCR)

Following the ligation of the adapters, the dynabeads were washed twice with 100 µl of 1×B&W buffer, again using the Magnetic Particle Collector (Invitrogen, for collecting the Dynabeads for each wash. The Dynabeads were then resuspended in 50 µl of EB buffer (Qiagen) and transferred to a fresh 1.5 ml microfuge tube. PCR was performing using Accuprime according to the Solexa preparation protocol (Illumina).

Example 12

Purification of PCR Products

The PCR products from, typically 1-25 reactions, may be pooled. The Dynabeads were then removed using the magnetic particle collector leaving the supernatant. The DNA was precipitated from the supernatant with isopropanol precipitation in the presence of GlycoBlue (Ambion) as co-precipitant as described in Example 7. After the final wash, the supernatant was discarded and the DNA resuspended in 40 µl of TE buffer (Qiagen)

The DNA was then electrophoresed in Novex 6% TBE PAGE gel, 1.0 mm, 5 well (Invitrogen cat. no. DC6264BOX) at 200 V for 30 minutes. The DNA standard size markers used were the 25 bp DNA Ladder and the Low DNA Mass Ladder (both from Invitrogen).

The DNA from the sample lanes of approximately 200-500 bp in sizes were excised and purified using the gel crush method.

Gel Crush Method

The excised gel pieces were collected into 0.6 ml microfuge tubes that have been pierced at the bottom with a 21G needle. The pierced 0.6 microfuge tube was placed into a 1.5 ml screw-cap microfuge tube and centrifuged at 16,100 g at 4° C. for 5 minutes. The centrifugation process shreds the gel slices which are then collected in the bottom of each 1.5 ml screw-cap microfuge tube.

200 µl of TE buffer (Qiagen) was added to each 1.5 ml screw-cap microfuge tube and resuspended well with the gel pieces using a pipette tip. The gel pieces should be completely immersed in the buffer.

The 1.5 screw-cap microfuge tubes containing the shredded gel pieces were frozen at −80° C. for 1-2 h, and then transferred directly to 37° C. for 16 h (maceration).

Following the maceration step, the contents of each 1.5 ml tube were transferred to a SpinX centrifuge filter (Corning) and centrifuged at 16,100 g, 4° C. for 10 minutes. The 1.5 ml tubes used for the maceration were rinsed by adding 200 µl of TE buffer (Qiagen) and subjected to a brief spin in a centrifuge to collect the TE buffer to the bottom of the tube.

The TE buffer used for the rinsing was then transferred into the corresponding SpinX centrifuge containing the gel pieces, resuspending the gel pieces by stirring briefly with the pipette tip. The TE buffer was collected by centrifuging again at 16,100 g, 4° C. for 20 minutes.

The filtrate was pooled and the DNA was precipitated with isopropanol and resuspended in 21 µl of TE buffer (Qiagen).

Alternatively the DNA may be purified with QIAEX II (Qiagen) according to the manufacturer's instructions, and eluted in 21 µl of TE buffer (Qiagen).

The quality and quantity of the recovered DNA may be determined by analysing a 1 ul of the recovered DNA with the 1000 DNA Chip kit (Agilent) according to the manufacturer's instructions. Alternatively, the quality and the quantity of the recovered DNA may be determined using picogreen fluorimetry (Quant-iT DNA assay kit, Molecular Probes) according to the manufacturer's instructions.

Example 13

Solexa Sequencing

Solexa sequencing (Illumina) was performed on the purified PCR products according to the manufacturer's instructions.

Example 14

Bioinformatics Analysis of the Sequenced Nucleic Acid Molecules Comprising the Paired Tags Following sequencing, the paired tags may be analysed using the software described in Chiu et al., (2006). The tags were mapped to the relevant reference genome using an alignment approach based on a compressed suffix array algorithm, in which the entire relevant genome was indexed as a reference database (Hon et al., 2007) and the tags were matched to the database. Alternatively, the tags may also be mapped to the relevant reference genome using the ELAND program provided by Solexa.

Figure 8:
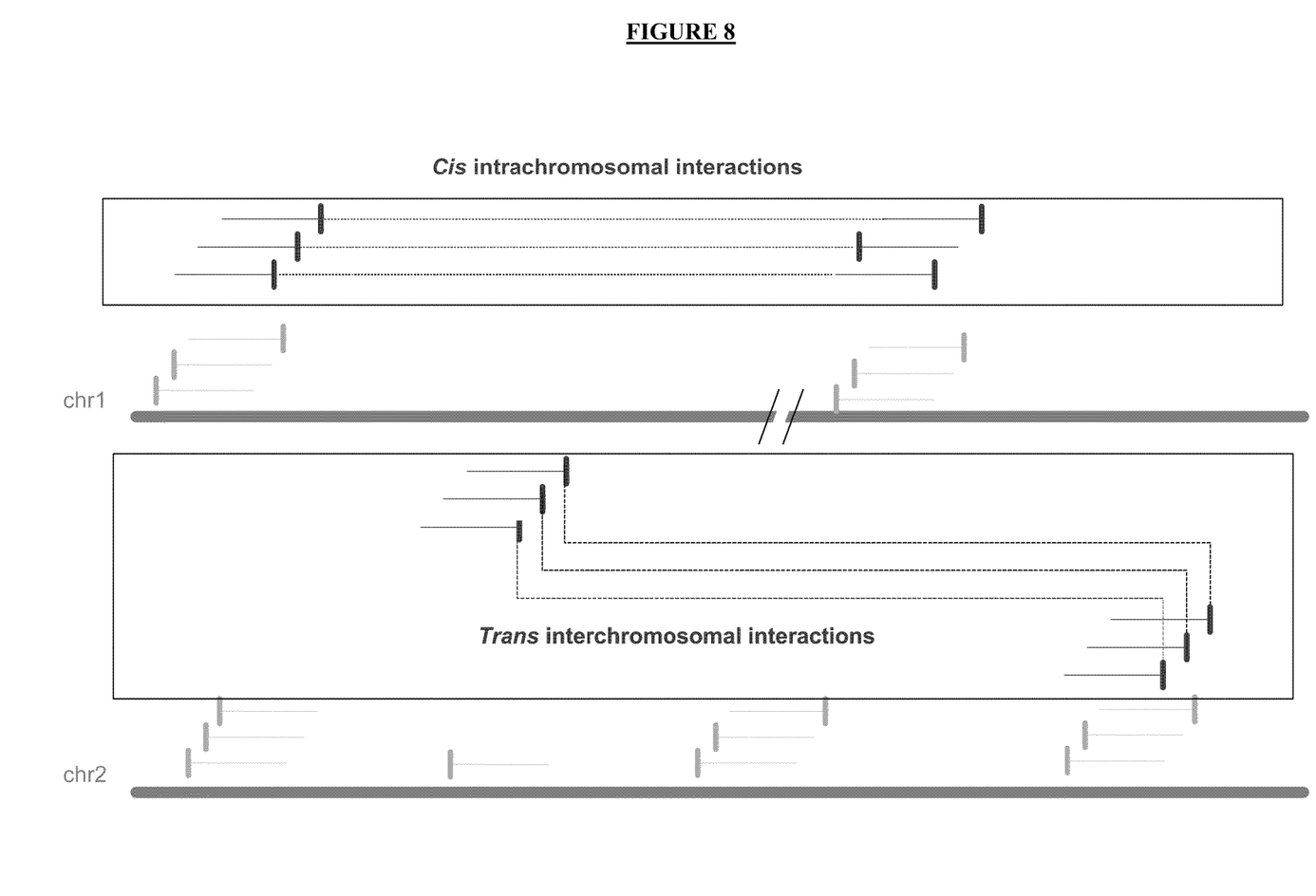

Following mapping, the sequenced information from each tag is extended by about 500 bp in the 5' to 3' direction to form a virtual DNA fragment. The virtual DNA fragment may be used for the analysis, by determining the frequency of tag mapped to a particular region (tag density). The unboxed tags in FIG. 8 illustrates that different regions have different map densities. Peaks can be identified as local maxima in the tag density, and binding sites can be identified as peaks with a high number of tags. High confidence interactions can be identified by finding multiple paired tags that map between two binding sites, and medium confidence interactions can be identified by finding multiple paired tags that map between a binding site and a non-binding site, as well as single paired tags that map between two binding sites. In addition, data obtained from the method of Ruan et al. (US 2007-0238101) may also be integrated with the data from the present invention to identify binding sites and interactions.

Figure 9:
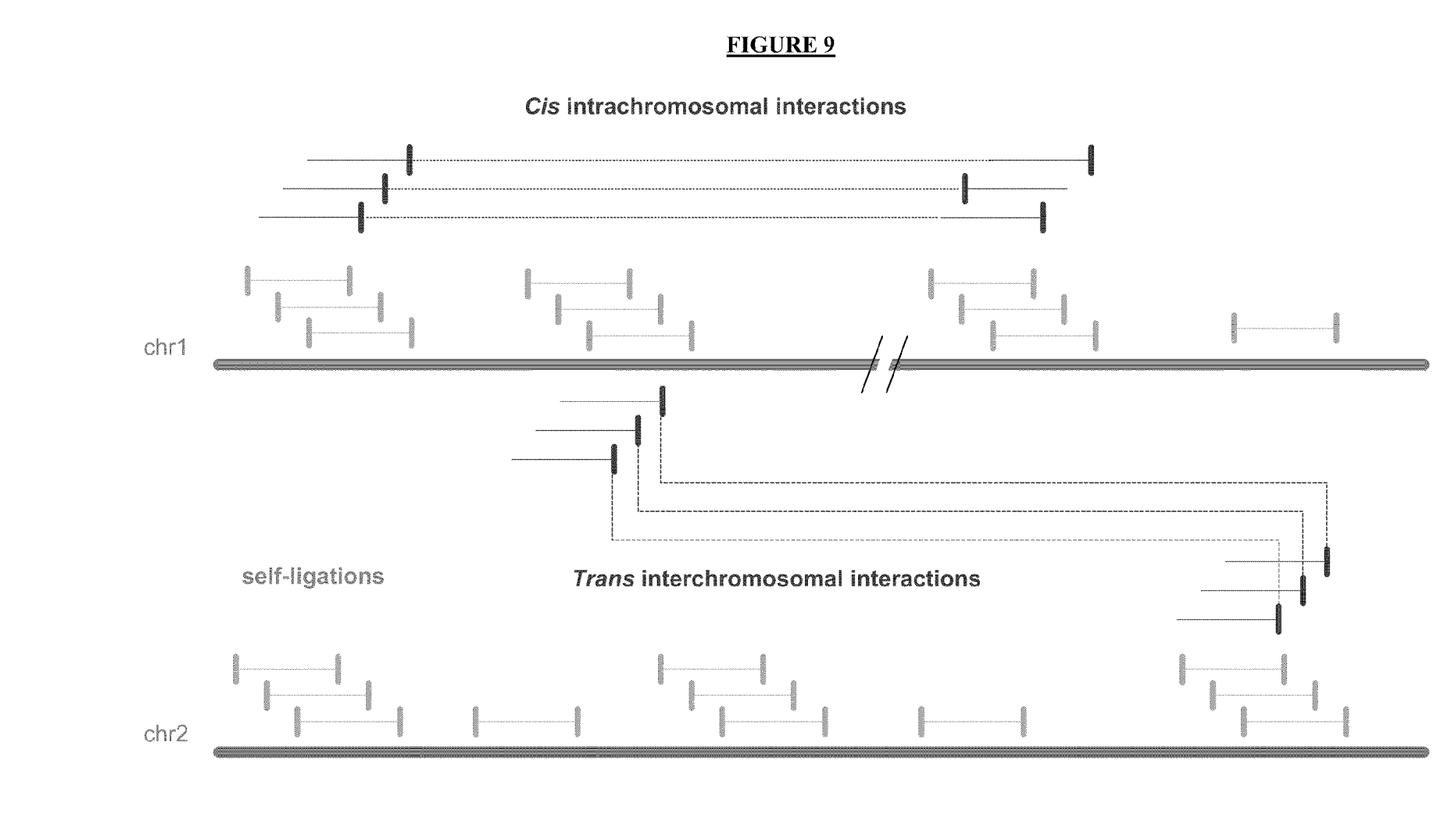
FIG. 9 is a diagram illustrating mapping of the tags from the method of Ruan et al. (US 2007-0238101) which identifies single binding sites (from self-ligations) as well as interactions from distal part of the same chromosome and interactions from different chromosomes. The vertical lines indicate the sequenced part of the tags that make up the paired tags of the isolated oligonucleotides of this prior art invention. The sequenced parts of the tags are used for mapping to the reference genome and the sequence is then extended by about 500 bp according to the sequence information of the reference genome to form virtual DNA fragments (firm horizontal lines). The dotted horizontal lines indicate the "span" of the interactions.

In comparison, the method described in Ruan et al. (US 2007-0238101 A1), the types of interactions identified include single binding sites (from self ligations) as well as interactions from distal parts of the same chromosome and interactions from different chromosomes (See FIG. 9).

It will be appreciated that various modifications and improvements may be made by a person skilled in the art without departing from the spirit and scope of the present invention.

REFERENCES

Carroll, J. S., Liu, X. S., Brodsky, A. S., Li, W. Meyer, C. A., Szary, A. J., Eeckhoute, J., Shao, W., Hestermann, E. V., Geistlinger, T. R., Fox, E. A., Silver, P. A. and Brown, M. (2005) Chromosome-wide mapping of estrogen receptor binding reveals long-range regulation requiring the forkhead protein FoxA1. Cell 122:33-43.

Cawley, S., Bekiranov, S., Ng, H. H., Kapranov, P., Sekinger, E. A., Kampa, D., Piccolboni, A., Sementchenko, V., Wong, B., Drenkow, J., Yamanaka, M., Patel, S., Brubaker, S., Tammana, H., Helt, G., Struhl, K. and Gingeras, T. R. (2004) Unbiased mapping of transcription factor binding sites along human chromosome 21 and 22 points to widespread regulation of noncoding RNAs. Cell 116:499-509.

Chiu, K. P., Wong, C-H., Chen, Q., Ariyaratne, P., Ooi, H.S., Wei, C-L., Sung, W-K. K. and Ruan, Y. (2006) PETTool, a software suite for comprehensive processing and managing of Paired-End ditag (PET) sequence data. BMC Bioinformatics 7:390.

Dekker, J., Rippe, K., Dekker, M. and Kleckner, N. (2002) Capturing chromosome conformation. Science 295:1306-1311.

Dostie, J., Richmond, T. A., Arnaout, R. A., Seizer, R. R., Lee, W. L., Honan, T. A., Rubio, E. D., Krumm, A., Lamb, J., Nusbaum, C., Green, R. D., Dekker, J. (2007) Chromosome conformation capture carbon copy (5C): A massively parallel solution for mapping interactions between genomic elements. Genome Research 16:1299-1309.

Haring, M., Offermann, S., Danker, T., Horst, I., Peterhansel, C. and Stam, M. (2007) Chromatin immunoprecipitation: optimization, quantitative analysis and data normalization. Plant Methods 3: 11.

Hon, W-K., Lam. T-K., Sadakane, K., Sung, W-K. and Yiu, S-M. (2007) A space and time efficient algorithm for constructing compressed suffix arrays. Algorithmica 48: 23-26.

Johnson, D. S., Mortazavi, A., Myers, R. M. and Wold, B. (2007) Genome-wide mapping of in vivo protein-DNA interactions. Science 316:1497-1502.

Orlando, V., Strutt, H. and Paro, R. (1997) Analysis of chromatin structure by in vivo formaldehyde cross-linking. Methods: A companion to methods in Enzymology 11: 205-214.

Ruan, Y., Fullwood, M. J. and Wei, C. L. US application 2007-0238101 A1.

Ruan, Y., Ng, P. Fullwood. M. J. and Lee, Y. U.S. application Ser. No. 11/449,872.

Sambrook and Russel, Molecular Cloning: A Laboratory Manual, Cold Springs Harbor Laboratory, New York (2001).

Shendure, J., Porreca, G. J., Reppas, N. B., Lin, X., McCutcheon, J. P., Rosenbaum, A. M., Wang, M. D., Zhang, K., Mitra, R. D. and Church, G. M. (2005) Accurate multiplex polony sequencing of an evolved genome. Science 309:1728-1732.

Simonis, M., Kous, P., Splinter, E., Moshkin, Y., Willemsen, R., de Wit, E., van Steensel, B. and de Laat, W. (2006) Nuclear organization of active and inactive chromatin domains uncovered by chromosome conformation capture on-chop (4C). Nature Genetics 38(11):1348-1354.

WO 2007/010252

WO 2007/091077

WO 2007/123744.

Talbert, P. B. and Henikoff, S. (2006) Spreading of silent chromatin: inaction at a distance. Nature Reviews 7:793-803.

Wei, C. L., Wu, Q., Vega, V. B., Chiu, K. P., Ng, P., Zhang, T., Shahab, A., Yong, H. C., Fu, Y., Weng, Z., Liu, J. J., Zhao, X. D., Chew, J-L., Lee, Y. L., Kuznetsov, V. A., Sung, W-K., Miller, L. D., Lim, B., Liu, E. T., Yu, Q., Ng, H. H. and Ruan, Y. (2006) A global map of p53 transcription-factor binding sites in the human genome. Cell 124: 207-219.

Zhao, Z., Tavoosidana, G., Sjölinder, M., Göndör, A., Mariano, P., Wang, S. Kanduri, C., Lezcano, M., Sandhu, K. S., Singh, U., Pant, V., Tiwari, V., Kurukuti, S. and Ohlsson, R. (2006) Circular chromosome conformation capture (4C) uncovers extensive networks of epigenetically regulated intra- and interchromosomal interactions. Nature Genetics 38(11):1341-1347.

The invention claimed is:

1. A method of preparing at least one isolated linear composite nucleic acid molecule comprising a first tag from a first nucleic acid molecule and a second tag from a second nucleic acid molecule, wherein the first and second nucleic acid molecules interact in a nucleic acid-protein complex and wherein the first and second tags are from different nucleic acid molecules; comprising the steps of:
  (i) providing at least one nucleic acid-protein complex comprising at least one first nucleic acid molecule interacting with at least one second nucleic acid molecule;
  (ii) (a) ligating at least one linker with at least one non-ligatable end to at least one end of the nucleic acid molecule(s) in the nucleic acid mixture; (b) converting the non-ligatable end(s) of the ligated linker(s) to make them ligatable; and (c) ligating the linker(s) to ligate the end(s) of the nucleic acid molecules to form at least one linker-ligated linear composite nucleic acid molecule comprising at least one linker between the two nucleic acid molecules;
  (iii) size selecting for linker-ligated linear composite nucleic and molecules comprising a first tag from a first nucleic acid molecule; and a second tag from a second nucleic acid molecule; and
  (iv) ligating at least one adapter to at least one end of the linker-ligated linear composite nucleic acid molecule(s) and isolating at least one linear composite nucleic acid molecule with both adapter(s) and linker(s) ligated, wherein the first and second tags of the linear composite nucleic acid molecule(s) are from different nucleic and molecules.

2. The method according to claim 1, wherein isolating the linear composite nucleic acid molecule(s) comprises using a binding system comprising at least two components, wherein at least one first component is coupled to the adapter, and at least one second component binds the first component to isolate the linear composite nucleic acid molecule(s).

3. The method according to claim 1, wherein isolating the linear nucleic acid molecule(s) comprises using a binding system comprising at least two components, wherein at least one first component is coupled to the linker, and at least one second component binds the first component to isolate the linear composite nucleic acid molecule(s).

4. The method according to claim 2, wherein the binding system comprises the components of streptavadin-biotin, avidin-biotin, protein-antibody and/or magnet-magnetic material.

5. The method according to claim 3, wherein the binding system comprises the components of streptavadin-biotin, avidin-biotin, protein-antibody and/or magnet-magnetic material.

6. The method according to claim 1, wherein step (ii) comprises:
  (a) ligating at least one dephosphorylated linker to at least one end of the nucleic acid molecules in the nucleic acid mixture;
  (b) phosphorylating the dephosphorylated end of the ligated linker(s); and
  (c) ligating the phosphorylated linker(s) to ligate the ends of the nucleic acid molecules to form at least one linker-ligated linear composite nucleic acid molecule comprising at least one linker between the ligated nucleic acid molecules.

7. The method according to claim 1, wherein step (ii) comprises:
  (a) ligating at least one dephosphorylated linker comprising at least one restriction enzyme site to at least one end of the nucleic acid molecules in the nucleic acid mixture;
  (b) cutting the ligated linker(s) with the restriction enzyme(s) for the site(s) to produce cohesive ends; and
  (c) ligating the cohesive ends of the linker(s) to ligate the ends of the nucleic acid molecules to form at least one linker-ligated linear composite nucleic acid molecule comprising at least one linker between the ligated nucleic acid molecules.

8. The method according to claim 1, wherein step (iii) comprises selecting for linear composite nucleic acid molecules of 200-500 bp.

9. The method according to claim 1, further comprising the step of amplifying the linear composite nucleic acid molecules.

10. The method according to claim 1, further comprising sequencing at least one linear composite nucleic acid molecules.

11. The method according to claim 10, wherein sequencing the linear composite nucleic acid molecules comprises sequencing from different regions of the linear composite nucleic acid molecules to obtain sequence information for the two tags.

12. The method according to claim 11, further comprising mapping the sequenced tags of the linear composite nucleic acid molecule to at least one reference sequence.

13. The method according to claim 12, wherein the reference sequence includes at least one sequence database.

14. The method according to claim 13, wherein the sequence database is at least one genome sequence database.

15. The method according to claim 1, wherein the nucleic acid-protein complex comprises chromatin.

16. The method according to claim 1, wherein the nucleic acid-protein complex is obtained by chromatin immunoprecipitation.

* * * * *